United States Patent [19]

Harandi et al.

[11] Patent Number: 4,973,778
[45] Date of Patent: Nov. 27, 1990

[54] CONTINUOUS SWING TUBULAR REACTOR-REGENERATOR

[75] Inventors: Mohsen N. Harandi, Sewell; Hartley Owen, Belle Mead, both of N.J.

[73] Assignee: Mobil Oil Corp., New York, N.Y.

[21] Appl. No.: 139,219

[22] Filed: Dec. 29, 1987

[51] Int. Cl.$^5$ .................. C07C 15/393; B01J 23/90
[52] U.S. Cl. .................. 585/407; 208/140; 585/412; 585/415; 585/417; 585/418; 585/419
[58] Field of Search .......... 208/140; 585/407, 412, 585/415, 417, 418, 419

[56] References Cited

U.S. PATENT DOCUMENTS

| | | | |
|---|---|---|---|
| 3,450,506 | 6/1969 | Guerrieri | 23/288 |
| 4,097,367 | 6/1978 | Haag et al. | 208/138 |
| 4,256,783 | 3/1981 | Takada et al. | 422/197 |
| 4,347,394 | 8/1982 | Detz et al. | 208/138 |
| 4,430,304 | 2/1984 | Spurrier et al. | 422/204 |
| 4,443,326 | 4/1984 | Field | 208/138 |
| 4,461,745 | 7/1984 | Ahlstrom, Jr. | 422/197 |
| 4,610,778 | 9/1986 | Graven | 208/89 |
| 4,652,360 | 3/1987 | Dessau | 208/138 |
| 4,806,699 | 2/1989 | Smith et al. | 585/407 |
| 4,835,336 | 5/1989 | McCullen | 208/138 |
| 4,854,089 | 4/1986 | Unmuth et al. | 208/138 |

Primary Examiner—Curtis R. Davis
Attorney, Agent, or Firm—Alexander J. McKillop; Charles J. Speciale; Robert B. Furr, Jr.

[57] ABSTRACT

A reactor system contained in a fired heater and a hydrocarbon upgrading process are disclosed for the concurrent conversion of a hydrocarbon feedstock and the regeneration of a deactivated catalyst. An effluent product slipstream from a set of operating reactors is used to hydrogen-regenerate deactivated catalyst in another set of reactors. Flue gas withdrawn from the fired heater stack is used as a purge and/or carrier gas during oxygen-regeneration of the catalyst.

24 Claims, 2 Drawing Sheets

CONTINUOUS SWING TUBULAR REACTOR-REGENERATOR

BACKGROUND OF THE INVENTION

This invention relates to hydrocarbon upgrading processes. In particular, the invention relates to a novel continuous swing reactor-regenerator design.

While previous reactor systems have employed piping configurations to periodically regenerate one of two or more catalyst beds while the remaining catalyst beds are on stream, none have suggested a continuous-swing tubular reactor system providing substantially isothermal reaction conditions and using a reactor effluent slipstream from a first set of parallel reactors to regenerate the catalyst in a second set of parallel reactors. Further, none have suggested a continuous-swing tubular reactor system wherein the tubular reactors are contained in a fired heater and flue gas from said heater is used as a catalyst regeneration gas.

For example, U.S. Pat. No. 3,450,506 to Guerrieri teaches an improved process of steam reforming using tubular reactors having a nickel oxide steam reforming catalyst integrally coated on the inside diameter of the tubular reactors.

U.S. Pat. No. 4,256,783 to Takada discloses a catalytic vapor phase oxidation reactor which comprises a fixed-bed shell and tube heat exchanger in which a tube bundle filled with at least one type of oxidizing catalyst is disposed in a shell. Heat transfer fluid is passed over the outside of the tubes in a multiplicity of zones to control the reaction temperature of the exothermic catalytic vapor phase oxidation reaction occuring inside the tubes.

U.S. Pat. No. 4,430,304 to Spurrier teaches a slab-shaped, high efficiency catalytic reformer comprising a plurality of structures forming a generally rectangular peripheral envelope spaced about one another to form annular regions. The interior annular region contains a catalytic bed and is regeneratively heated on one side by hot combustion gases and on the other by the gaseous products of the reformation.

U.S. Pat. No. 4,461,745 to Ahlstrom discloses a self-regenerating catalytic reactor. The reactor is of the shell and tube type, wherein the head on the first end of the reactor is divided by a partition. A reactant, for example oxygen, is passed into one side of the divided head, passed through the tubes containing catalyst on one side of the reactor which are available to that portion of that head. Upon exiting into the head at the opposite end of the reactor the reactant oxygen is mixed with another reactant, for example a chlorinated hydrocarbon, and fed into tubes on the other end of the reactor, which also contains catalyst, and wherein the oxidation of the chlorinated hydrocarbon occurs. The product gases exit on the side of the divided head opposite the oxygen inlet at the first end of the reactor. A heat exchange medium surrounds the tubes and circulates within the shell to either heat or cool the tubes as necessary. When the catalyst employed in the reaction becomes coated with carbonaceous material, the flow is reversed and the oxygen fed into the side of the reactor containing the deactivated catalyst. This design does not suggest the use of a reactor effluent stream to regenerate the catalyst.

SUMMARY OF THE INVENTION

The present invention comprises a novel continuous swing tubular reactor-regenerator system and its associated hydrocarbon upgrading processes. By regenerating one or more sets of catalyst-filled reactors while reacting a hydrocarbon feed in one or more other sets, the continuous swing tubular reactor-regenerator system can continuously process a hydrocarbon feedstream without interrupting unit operation to regenerate the catalyst. Further, the continuous swing tubular reactor-regenerator system provides its own hydrogen-rich regeneration gas source, eliminating the need for an external hydrogen source during hydrogen regeneration. The system also uses furnace flue gas as purge gas and inert carrier gas during oxygen regeneration to eliminate or substantially reduce the need for an external source of inert gas.

The reactor system comprises longitudinally extensive catalyst-filled tubular reactor sets positioned inside a fired heater shell with said tubular reactor sets connected to peripheral processing equipment located outside the heater shell for separating a hydrogen-rich slipstream from the effluent product stream of an operating reactor set to regenerate the deactivated catalyst in a second reactor set.

Longitudinally extensive tubular reactors provide a relatively high ratio of heat transfer area to volume. Inside the fired heater, the outer tube walls are in constant contact with hot flue gases, enabling the tubular reactors to provide a substantially isothermal reaction environment. The tubular reactor design is therefore particularly well suited for endothermic reactions, such as the catalytic aromatization and oligomerization of hydrocarbons, which achieve their greatest selectivity within a relatively narrow range of temperatures.

Both soft and hard coke accumulate on the catalyst particles and block access to the pores. Soft coke may be removed by contacting the catalyst with a hydrogen-rich gas. Hard coke, on the other hand, must be removed by a controlled burn. This controlled burn is generally accomplished by passing an inert gas containing a small, closely regulated amount of oxygen over the catalyst bed.

To remove soft coke from the catalyst in a conventional fixed-bed reactor by hydrogen regeneration, the reactor must be taken off-stream and treated with hydrogen-rich gas from an external source. In contrast, the continuous swing reactor-regenerator system regenerates a first bank of catalyst-filled reactors using a slipstream separated from the effluent of a second bank of catalyst-filled reactors.

To burn off hard coke from the catalyst in a conventional fixed-bed reactor, the system must first be purged with an inert gas such as nitrogen. After the system is purged, a stream of inert gas in heated, mixed with a controlled amount of oxygen and charged to the reactor. To prevent irreversible damage to the catalyst due to overheating, oxygen injection is regulated to maintain the catalyst below a predetermined maximum temperature. The reactor bed temperature profile is monitored by a series of thermocouples spaced longitudinally through the bed.

The coke deposition, as well as the regeneration gas flow, may not be uniform across the width of the conventional fixed-bed reactor. As a result, the temperature profile across the width of the reactor bed may vary widely. Hot spots, undetected by the thermocouples, may cause an irreversible loss of catalytic activity.

In the continuous swing tubular reactor-regenerator system, on the other hand, each catalyst bed is relatively narrow. Catalyst temperature inside the reactor tubes is easily controlled both by adjusting the surrounding burners and by controlling the amount of oxygen in the regeneration gas. As a result, variations in temperature across the catalyst bed are minimized.

Further, the continuous swing tubular reactor-regenerator system can use flue gas from the furnace to purge the system before oxygen regeneration and as an inert carrier gas during oxygen regeneration. Using hot flue gas as an inert carrier gas increases the energy efficiency of the process unit while reducing the requirements for purchased inert gas.

The peripheral processing equipment associated with the continuous swing reactor-regenerator system separates the effluent from the operating reactor set into a hydrogen-rich gas stream and a product stream. During hydrogen regeneration, a portion of the hydrogen-rich gas stream is charged to an off-stream reactor set to regenerate the deactivated catalyst.

The hydrocarbon upgrading process of the present invention converts aliphatic hydrocarbons to aromatic hydrocarbons by contacting the aliphatic hydrocarbon mixture with a catalyst in sets of tubular reactors positioned inside a fired heater. The resulting product stream is separated into two streams: a hydrogen-rich stream containing hydrocarbons having fewer than three carbon atoms and a product stream having greater than two carbon atoms. The hydrogen-rich stream may then be charged to another set of tubular reactors positioned inside the fired heater to hydrogen regenerate the catalyst contained therein. The product stream is further processed as described above. A stream of flue gas may also be withdrawn from the fired heater stack, compressed, blended with oxygen, an inert gas, or a mixture thereof, and charged to another set of tubular reactors positioned inside the fired heater shell to oxygen regenerate the catalyst contained therein. To minimize catalyst permanent deactivation the flue gas may optionally be cooled to separate water from the regeneration gas upstream of the tubular reactor.

DETAILED DESCRIPTION

Figure 1:
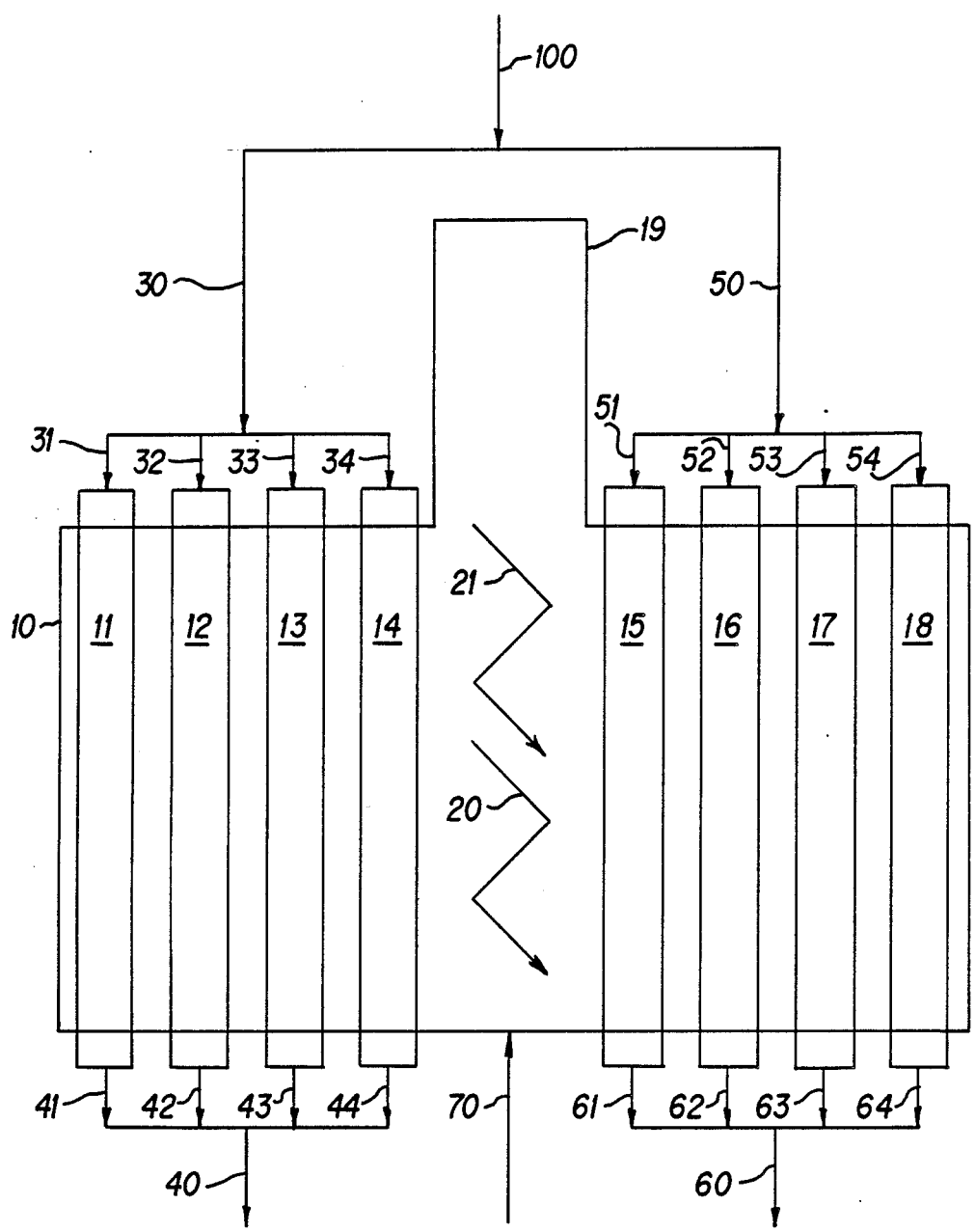
FIG. 1 is a simplified schematic diagram of the fired heater section of the continuous swing tubular reactor-regenerator system.

Referring to FIG. 1, the heater shell 10 houses tubular catalyst-filled reactors 11, 12, 13, 14, 15, 16, 17, and 18. The heater shell is lined with a refractory insulation and is equipped with draft control devices such that the burners positioned inside the heater shell firing gas, oil, or a mixture thereof maintain the reactant mixture flowing through the tubular reactors at a temperature of between about 800° and about 1600° F., preferably between about 1000° and about 1200° F. While pressure decreases slightly between the inlets and the outlets of the tubular reactors, the outlet pressure is maintained at between about 0 and about 300 psig, preferably between about 30 and about 150 psig. The WHSV (weight hourly space velocity) of the reactant mixture is maintained at between about 0.1 and about 500 hr$^{-1}$, preferably between about 0.2 and 20 hr$^{-1}$. For the purpose of this disclosure, the weight hourly space velocity is defined as the number of pounds of reactant charged to the reactor set per hour divided by the number of pounds of catalyst contained in the reactor set.

The eight tubular reactors shown are divided into two sets of four reactors in parallel. While sets of four reactors are shown, the reactor sets may contain between one and one hundred tubular reactors each, preferably between three and twenty. Further, while two sets of reactors are shown, up to ten sets of reactors may be used.

Feed to each reactor set is divided among parallel reactors. The primary feed header 100 divides into secondary feed headers 30 and 50. Secondary feed header 30 is subdivided into inlet piping segments 31, 32, 33, and 34. Secondary feed header 50 is subdivided into inlet piping segments 51, 52, 53, and 54. Inlet piping segments 31, 32, 33, and 34 feed tubular reactors 11, 12, 13, and 14, respectively. Inlet piping segments 51, 52, 53, and 54 feed tubular reactors 15, 16, 17, and 18, respectively. Similarly, tubular reactors 11, 12, 13, and 14 discharge into outlet piping segments 41, 42, 43, and 44, respectively, which then discharge into reactor outlet header 40. Tubular reactors 15, 16, 17, and 18 discharge into reactor outlet piping segments 61, 62, 63, and 64, respectively, which then discharge into reactor effluent header 60.

Combustion products from the burners together with a controlled amount of excess air pass first around the tubular reactors, then over the steam generation coils 20 and finally over the air preheat coils 21 before exiting the heater stack 19. To maximize heater efficiency, hot flue gas may be heat-exchanged to generate steam and to preheat burner combustion air.

Figure 2:
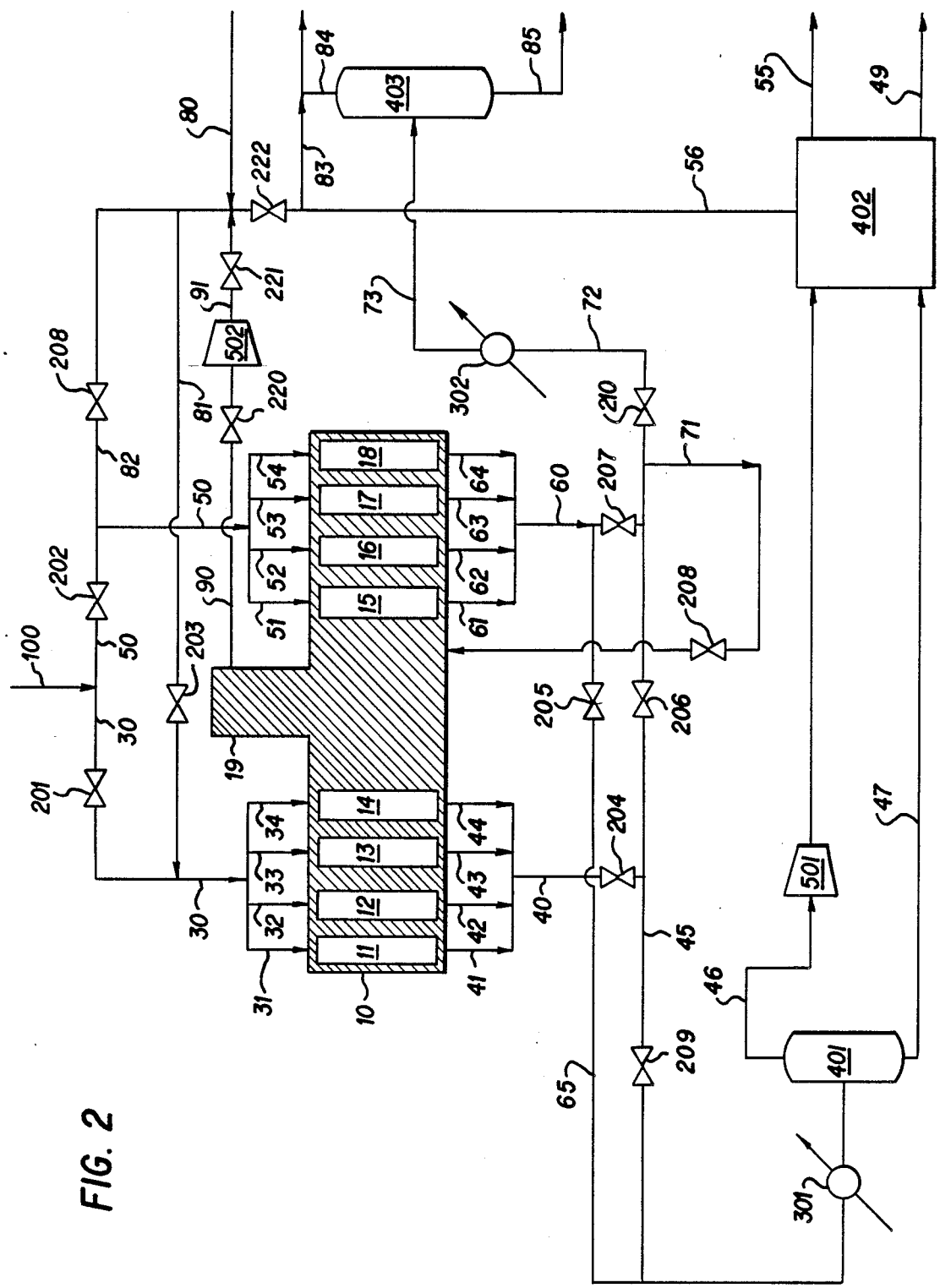
FIG. 2 is a simplified schematic diagram of the continuous swing tubular reactor-regenerator system.

Referring now to FIG. 2, an aliphatic hydrocarbon mixture is charged to the continuous swing tubular reactor-regenerator system through primary feed header 100. By setting the appropriate valves, either bank of reactors may be regenerated while the other bank is processing hydrocarbon feed on stream. Alternatively, in periods of high product demand, both banks of reactors may process hydrocarbon feed on stream.

Reaction-Hydrogen Regeneration Scheme 1

In Scheme 1, a first tubular reactor bank 11, 12, 13 and 14 reacts the aliphatic hydrocarbon feedstream to form an aromatic hydrocarbon effluent stream, while the deactivated catalyst in a second tubular reactor bank 15, 16, 17 and 18 is regenerated.

An aliphatic hydrocarbon mixture is charged to the continuous swing tubular reactor-regenerator system through primary feed header 100. Valve 202 in secondary feed header 50 is closed and the hydrocarbon feed mixture passes through open valve 201, secondary feed header 30 and reactor inlet piping segments 31, 32, 33, and 34 into reactors 11, 12, 13, and 14. The product mixture, now rich in aromatic hydrocarbons, flows out of tubular reactors 11, 12, 13, and 14 into reactor outlet piping segments 41, 42, 43, and 44, respectively. The mixture then flows into reactor effluent header 40 and through open valve 204 into line 45. Valve 206 is closed and the mixture flows through open valve 209 and into reactor effluent cooler 301. The chilled reactor effluent mixture then flows to knockout drum 401 where it is split into an overhead stream and a bottom stream. The overhead stream which flows out of the knockout drum 401 through line 46 is rich in hydrogen and C$_2$ and lighter hydrocarbons. The bottom stream which flows out of the knockout drum 401 through line 47 is rich in aromatic hydrocarbons. The overhead stream in line 46 is compressed in compressor 501. The high pressure stream from line 48, together with the knockout drum bottoms from line 47 enters product fractionation section 402, where it is separated into gasoline which flows out of the fractionation section 402 through line 49, liquified petroleum gas which flows out of the fractionation section 402 through line 55, and a mixture of hydrogen and $C_2$ and lighter hydrocarbons leaving the fractionation section 402 through line 56. Gasoline and LPG are piped off the unit for further product treatment and storage. The reaction occurring in the first set of tubular reactors may produce a greater quantity of hydrogen rich gas than is required for the regeneration of the second bank of tubular reactors. This excess product in line 83 is combined with other waste gases from the process and may be burned as fuel gas or processed in other units requiring a hydrogen rich feed stream. The remaining hydrogen rich gas mixture may optionally be mixed with a regeneration gas supplied through line 80.

Valves 202 and 203 are closed causing the mixture in line 82 to flow through open valve 208, through secondary feed header 50, inlet piping segments 51, 52, 53, and 54, and through tubular reactors 15, 16, 17, and 18, respectively. The regeneration gas mixture leaves the reactors through outlet piping segments 61, 62, 63, and 64, and flows into reactor outlet header 60. Valve 207 is open while valve 206 is closed, directing the spent regeneration gas mixture in line 72 through spent regeneration gas cooler 302. The chilled gas mixture in line 73 flows to knockout drum 403. The bottoms product leaving knockout drum 403 through line 85 contains high molecular weight hydrocarbons from the spent catalyst and is routed to the refinery catalytic cracking or crude unit. The overhead stream leaving knockout drum 403 through line 84 is rich in hydrogen and light hydrocarbon gases and is combined with the excess product stream flowing through line 83 to be burned as fuel gas or routed to a process unit requiring a charge stream rich in hydrogen.

To recycle a portion of the spent regeneration gas, valve 205 may be opened to allow a slipstream of spent regeneration gas in line 65 to flow back into reactor effluent cooler 301.

Reaction-Regeneration Scheme 2

In Scheme 2, a first tubular reactor bank 11, 12, 13 and 14 is regenerated while a second tubular reactor bank 15, 16, 17 and 18 reacts the aliphatic hydrocarbon feedstream. A mixture of aliphatic hydrocarbons is fed to the unit through primary feed header 100. Valves 201 and 208 are closed and valve 202 is open, directing flow through secondary feed header 50, reactor inlet piping segments 51, 52, 53, and 54, and tubular reactors 15, 16, 17, and 18, respectively. The aromatic product mixture exits through effluent piping segments 61, 62, 63, and 64 and flows through reactor effluent header 60. Valve 207 is closed, and the reactor effluent mixture in line 65 flows through open valve 205 to the reactor effluent cooler 301. The chilled mixture is fed to knockout drum 401 and processed through compressor 501 and product fractionation section 402 as described above.

To regenerate the first bank of reactors, valves 201 and 208 are closed, while valve 203 is open. The regeneration gas mixture in line 81 flows through open valve 203, through secondary feed header 30, inlet piping segments 31, 32, 33, and 34 and through reactors 11, 12, 13, and 14, respectively. The spent regeneration gas mixture exits the reactors through reactor effluent piping segments 41, 42, 43, and 44, respectively, and flows into reactor effluent header 40. Valve 204 is open and valve 209 is closed, directing the spent regeneration gas mixture in line 72 through open valves 206 and 210, to the spent regeneration gas cooler 302. The chilled mixture in line 73 is fed to the knockout drum 403 where it is processed as described above.

Reaction-Regeneration Scheme 3

In Scheme 3, a first tubular reactor bank 11, 12, 13 and 14 reacts the aliphatic hydrocarbon feed stream to form an aromatic hydrocarbon effluent stream, while hard coke is burned off the catalyst in a second tubular reactor bank 15, 16, 17 and 18.

An aliphatic hydrocarbon mixture is charged to the continuous swing tubular reactor-regenerator system through primary feed header 100. Valve 202 in secondary feed header 50 is closed and the hydrocarbon feed mixture passes through open value 201, secondary feed header 30 and reactor inlet piping segments 31, 32, 33 and 34 into reactors 11, 12, 13 and 14, respectively. The product mixture, now rich in aromatic hydrocarbons, flows out of tubular reactors 11, 12, 13 and 14 into reactor outlet piping segments 41, 42, 43 and 44, respectively. The mixture then flows into reactor effluent header 40 and through open valve 204 into line 45. Valve 206 is closed and the mixture flows through open valve 209 and into reactor effluent cooler 301. The chilled reactor effluent mixture then flows to knockout drum 401 where it is split into an overhead stream and a bottom stream. The overhead stream which flows out of the knockout drum 401 through line 46 is rich in hydrogen and $C_2$ and lighter hydrocarbons. The bottom stream which flows out of knockout drum 401 through line 47 is rich in aromatic hydrocarbons. The overhead stream in line 46 is compressed in compressor 501. The high pressure liquid stream from line 48, together with the knockout drum bottoms from line 47, enters the product fractionation section 402 where it is separated into gasoline which flows out of the fractionation section 402 through line 49, liquified petroleum gas which flows out of the fractionation section 402 through line 55 and a mixture of hydrogen and $C_2$ and lighter hydrocarbons leaving the fractionation section 402 through line 56. Gasoline and LPG are piped off the unit for further product treatment and storage. Valve 222 is closed and the hydrogen-rich gas stream in line 56 flows through line 83 and may be burned as fuel gas or processed in other units requiring a hydrogen-rich feedstream.

A stream of flue gas is withdrawn from the heater stack 19 and flows in line 90 through open valve 220 to compressor 502. The compressed flue gas flows in line 91 through open valve 221 and enters line 82 where it may be mixed with oxygen, an inert gas such as nitrogen, or a mixture of oxygen and inert gases. Valve 222 is closed. The flow rates through lines 91 and 80 and the oxygen content of the gas flowing through line 80 are regulated such that the regeneration gas mixture flowing through line 82 contains the desired amount of oxygen. As detailed above, the oxygen content in the regeneration gas mixture is controlled such that the catalyst does not exceed a specified temperature during the hard coke burn.

Valve 208 is open while valve 202 is closed and the regeneration gas mixture flows from line 82 into secondary reactor inlet header 50 and reactor inlet piping segments 51, 52, 53 and 54. The regeneration gas mixture flows from the reactor inlet piping segments into tubular reactors 15, 16, 17 and 18, respectively. The hard coke which is deposited on the catalyst burns in the presence of the oxygen-containing gas. The spent regeneration gas mixture flows out of the reactors through outlet piping segments 61, 62, 63 and 64 into reactor effluent header 60. Valves 206 and 210 are closed. The spent regeneration gas mixture flows through open valve 207 into line 71 and through open valve 208 into the fired heater box 10.

Reaction-Regeneration Scheme 4

In Scheme 4, the hard coke is burned off the catalyst in a first tubular reactor bank 11, 12, 13 and 14, while a second tubular reactor bank 15, 16, 17 and 18 reacts the aliphatic hydrocarbon feedstream. A mixture of aliphatic hydrocarbons is fed to the unit through primary feed header 100. Valves 201 and 208 are closed and valve 202 is open, directing flow through secondary feed header 50, reactor inlet piping segments 51, 52, 53 and 54, and tubular reactors 15, 16, 17 and 18, respectively. The aromatic product mixture exits through effluent piping segments 61, 62, 63 and 64 and flows through reactor effluent header 60. Valve 207 is closed, and the reactor effluent mixture in line 65 flows through open valve 205 to the reactor effluent cooler 301. The chilled mixture is fed to knockout drum 401 and processed through compressor 501 and product fractionation section 402 as described above.

A stream of flue gas is withdrawn from the heater stack 19 and flows in line 90 through open valve 220 to compressor 502. The compressed flue gas flows in line 91 through open valve 221 and enters line 82 where it may be mixed with oxygen, an inert gas such as nitrogen or a mixture of oxygen and inert gases. Valve 222 is closed. The flow rates through lines 91 and 80 and the oxygen content of the gas flowing through line 80 are regulated such that the regeneration gas mixture flowing through line 82 contains the desired amount of oxygen. As detailed above, the oxygen content in the regeneration gas mixture is controlled such that the catalyst does not exceed a specified temperature during the hard coke burn.

Valve 203 is open while valve 208 is closed and the regeneration gas mixture flows from line 81 into secondary reactor inlet header 30 and reactor inlet piping segments 31, 32, 33 and 34. The regeneration gas mixture flows from the reactor inlet piping segments into tubular reactors 11, 12, 13 and 14, respectively. The hard coke which is deposited on the catalyst burns in the presence of the oxygen-containing gas. The spent regeneration gas mixture flows out of the reactors through outlet piping segments 41, 42, 43 and 44 into reactor effluent header 40. Valves 207, 209 and 210 are closed. The spent regeneration gas mixture flows through open valve 204 into line 45. Valve 206 is open and the mixture flows into line 71, through open valve 208 into the fired heater box 10.

Reaction Scheme 5

During periods of high product demand, both reactor banks may be operated in parallel to maximize unit throughput.

An aliphatic hydrocarbon feed mixture enters the unit through the primary feed header 100. Valves 201 and 202 are open, while valves 203 and 208 are closed. Thus, the flow is split between the secondary feed headers 30 and 50. Valves 205 and 210 are closed, while valves 204, 206, 207, and 209 are open. The combined reactor effluent flows through line 45 and is processed through reactor effluent cooler 301, knockout drum 401, compressor 501, and product fractionation section 402, as described above, except that the total volume of the hydrogen-rich light hydrocarbon stream in line 56 leaves the unit as effluent gas through line 83.

Catalysts

In a preferred embodiment, the catalyst in the aforementioned tubular reactors is a zeolite catalyst having a Constraint Index of between about 1 and about 12. Examples of such zeolite catalysts include ZSM-5, ZSM-11, ZSM-12, ZSM-23 and ZSM-35.

Zeolite ZSM-5 and the conventional preparation thereof are described in U.S. Pat. No. 3,702,886, the disclosure of which is incorporated herein by reference. Other preparations for ZSM-5 are described in U.S. Pat. Nos. Re. 29,948 (highly siliceous ZSM-5); 4,100,262 and 4,139,600, the disclosure of these is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. Another preparation of ZSM-35 is described in U.S. Pat. No. 4,107,195, the disclosure of which is incorporated herein by reference.

The production of aromatics in the presence of a gallium-containing zeolite catalyst is disclosed in U.S. Pat. No. 4,350,835 and U.S. Pat. No. 4,686,312, both of which are incorporated by reference as if set forth at length herein.

Zinc-containing zeolite catalysts are useful in the present invention, for example, U.S. Pat. No. 4,392,989 and U.S. Pat. No. 4,472,535, both of which are incorporated by reference as if set forth at length herein.

Catalysts such as ZSM-5 combined with a Group VIII metal described in U.S. Pat. No. 3,856,872, incorporated by reference as if set forth at length herein, are also useful in the present invention.

The members of the class of zeolites useful herein have an effective pore size of generally from about 5 to about 8 Angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering of the rings or pore blockage may render these zeolite ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. The method by which the Constraint Index is determined is described in U.S. Pat. No. 4,016,218, incorporated herein by reference for details of the method. U.S. Pat. No. 4,696,732 discloses Constraint Index values for typical zeolite materials and is incorporated by reference as if set forth at length herein.

Hydrocarbon upgrading reactions compatible with the process of the present invention include the conversion of aliphatic hydrocarbons to aromatic hydrocarbons. The following representative U.S. patents detail the feed compositions and process conditions for these reactions.

U.S. Pat. No. 3,756,942, incorporated by reference as if set forth at length herein, discloses a process for the preparation of aromatic compounds in high yields which involves contacting a particular feed consisting essentially of mixtures of paraffins and/or olefins, and/or naphthenes with a crystalline aluminosilicate of the ZSM-5 type under conditions of temperature and space velocity such that a significant portion of the feed is converted directly into aromatic compounds. In particular, Examples 32-37 show the reactor effluent product to contain between about 2.0 and about 5.0 wt. % hydrogen.

U.S. Pat. No. 3,759,821, incorporated by reference as if set forth at length herein, discloses a process for upgrading catalytically cracked gasoline.

U.S. Pat. No. 3,760,024, incorporated by reference as if set forth at length herein, teaches a process for the preparation of aromatic compounds involving contacting a feed consisting essentially of $C_2$-$C_4$ paraffins and/or olefins with a crystalline aluminosilicate of the ZSM-5 type.

The feedstocks and process conditions disclosed in the above three patents are suitable for use with the method and apparatus of the present invention. However, in the most preferred embodiment, the feedstock comprises a mixture of aliphatic hydrocarbons rich in $C_3$-$C_5$ paraffins which are converted to aromatics under the reaction conditions employed predominately by the reactions of cyclization, dehydrocyclization, and dehydrogenation so that a product stream containing aromatics and free hydrogen is produced. The reaction conditions may also be varied to maximize the yield of olefins and aromatics.

What is claimed is:

1. An integrated process for upgrading aliphatic hydrocarbons comprising the steps of:
   (a) providing a first and a second set of zeolite catalyst containing longitudinally extensive tubular reactors positioned within a process furnace to permit direct contact between the outer walls of said tubular reactors and hot process furnace flue gases;
   (b) interconnecting said longitudinally extensive tubular reactors of step (a) to selectively admit aliphatic hydrocarbons, hydrogen-rich regeneration gas, or oxygen-containing regeneration gas to one or both sets of said longitudinally extensive tubular reactors;
   (c) flowing aliphatic hydrocarbons to said first set of tubular reactors under substantially isothermal aromatization conversion conditions whereby a product mixture rich in aromatic hydrocarbons is evolved;
   (d) separating said product mixture of step (c) into two streams, a hydrogen-rich stream containing hydrocarbons having fewer than three carbon atoms and a second stream containing hydrocarbons having greater than two carbon atoms; and
   (e) charging said hydrogen-rich gas stream of step (d), to said second longitudinally extensive tubular reactor set whereby said zeolite catalyst contained therein is hydrogen-regenerated under substantially isothermal conditions.

2. The process of claim 1 wherein said zeolite catalyst has a Constraint Index of from about 1 to about 12.

3. The process of claim 2 wherein said substantially isothermal aromatization conversion condition include temperature from about 800° F. to about 1600° F.

4. The process of claim 2 wherein said aliphatic hydrocarbons of step (c) contact said zeolite catalyst at a weight hourly space velocity of from about 0.1 to about 500 $hr^{-1}$.

5. The process of claim 3 further wherein said aromatization conversion conditions include pressure of from about 0 psig to 300 psig.

6. The process of claim 2 wherein said zeolite catalyst has the structure of at least one selected from the group consisting of ZSM-5, ZSM-11, ZSM-12, ZSM-22, ZSM-23 and ZSM-35.

7. The process of claim 6 wherein said zeolite catalyst contains at least one metal selected from the group consisting of gallium, platinum, and zinc.

8. An integrated process for upgrading aliphatic hydrocarbons comprising the steps of:
   (a) providing a first and a second set of zeolite catalyst containing longitudinally extensive tubular reactors positioned within a process furnace to permit direct contact between the outer walls of said tubular reactors and hot process furnace flue gases;
   (b) interconnecting said longitudinally extensive tubular reactors of step (a) to selectively admit aliphatic hydrocarbons, hydrogen-rich regeneration gas, or oxygen-containing regeneration gas to one or both sets of said longitudinally extensive tubular reactors;
   (c) flowing aliphatic hydrocarbons to said first set of tubular reactors under substantially isothermal aromatization conversion conditions to evolve a product mixture rich in aromatic hydrocarbons whereby said zeolite catalyst is progressively deactivated by the deposition of coke on said zeolite catalyst;
   (d) discontinuing flow said of aliphatic hydrocarbons to said first set of tubular reactors;
   (e) flowing aliphatic hydrocarbons to said second set of tubular reactors under substantially isothermal aromatization conversion conditions to evolve a product mixture rich in aromatic hydrocarbons and hydrogen;
   (f) separating said product mixture of step (e) into two streams, a hydrogen-rich stream containing hydrocarbons having fewer than three carbon atoms and a second stream containing hydrocarbons having greater than two carbon atoms;

(g) charging hydrogen-rich gas stream of step (f) above, to said first set of zeolite catalyst containing tubular reactors under substantially isothermal regeneration conditions to hydrogen-regenerate said zeolite catalyst.

9. The process of claim 8 wherein said zeolite catalyst has a Constraint Index of from about 1 to about 12.

10. The process of claim 9 wherein said substantially isothermal aromatization conversion condition include temperature from about 800° F. to about 1600° F.

11. The process of claim 9 wherein said aliphatic hydrocarbons of step (c) contact said zeolite catalyst at a weight hourly space velocity of from about 0.1 to about 500 hr$^{-1}$.

12. The process of claim 9 further wherein said aromatization conversion conditions include pressure of from about 0 psig to 300 psig.

13. The process of claim 9 wherein said zeolite catalyst has the structure of at least one selected from the group consisting of ZSM-5, ZSM-11, ZSM-12, ZSM-22, ZSM-23 and ZSM-35.

14. The process of claim 13 wherein said zeolite catalyst contains at least one metal selected from the group consisting of gallium, platinum, and zinc.

15. An integrated process for upgrading aliphatic hydrocarbons comprising the steps of:

(a) providing a first and a second set of zeolite catalyst containing longitudinally extensive tubular reactors positioned within a process furnace to permit direct contact between the outer walls of said tubular reactors and hot process furnace flue gases;

(b) interconnecting said longitudinally extensive tubular reactors of step (a) to selectively admit aliphatic hydrocarbons, hydrogen-rich regeneration gas, or oxygen-containing regeneration gas to one or both sets of said tubular reactors;

(c) flowing aliphatic hydrocarbons to said first set of tubular reactors under substantially isothermal aromatization conversion conditions to evolve a product mixture rich in aromatic hydrocarbons whereby said zeolite catalyst is progressively deactivated by the deposition of coke on said zeolite catalyst;

(d) discontinuing flow said of aliphatic hydrocarbons to said first set of tubular reactors;

(e) flowing aliphatic hydrocarbons to said second set of tubular reactors under substantially isothermal aromatization conversion conditions to evolve a product mixture rich in aromatic hydrocarbons and hydrogen;

(f) withdrawing hot flue gas from said process furnace of step (a) and charging said flue gas to said first set of longitudinally extensive tubular reactors to oxidatively regenerate said zeolite catalyst contained therein under substantially isothermal conditions.

16. The process of claim 15 further comprising compressing said hot flue gas of step (f) after withdrawing said flue gas from said process furnace and before charging said flue gas to said first set of longitudinally extensive tubular reactors.

17. The process of claim 16 further comprising mixing said flue gas with an oxygen-containing stream before charging said flue gas to said first set of longitudinally extensive tubular reactors.

18. The process of claim 16 further comprising mixing said flue gas with an inert gas before charging said flue gas to said first set of longitudinally extensive tubular reactors.

19. The process of claim 15 wherein said zeolite catalyst has a Constraint Index of from about 1 to about 12.

20. The process of claim 19 wherein said substantially isothermal aromatization conversion condition include temperature from about 800° F. to about 1600° F.

21. The process of claim 19 wherein said aliphatic hydrocarbons of step (c) contact said zeolite catalyst at a weight hourly space velocity of from about 0.1 to about 500 hr$^{-1}$.

22. The process of claim 20 further wherein said aromatization conversion conditions include pressure of from about 0 psig to 300 psig.

23. The process of claim 19 wherein said zeolite catalyst has the structure of at least one selected from the group consisting of ZSM-5, ZSM-11, ZSM-12, ZSM-22, ZSM-23 and ZSM-35.

24. The process of claim 23 wherein said zeolite catalyst contains at least one metal selected from the group consisting of gallium, platinum, and zinc.

* * * * *